(12) United States Patent
Heasley (10) Patent No.: US 6,981,870 B2
(45) Date of Patent: Jan. 3, 2006

(54) RUBBER DAM CLAMPS RETAINED BY ADHESION AND IMPROVED FRICTIONAL FORCES

(76) Inventor: John M. Heasley, 1614 Dover St., Iowa City, IA (US) 52240

(*) Notice: Subject to any disclaimer, the term of this patent is extended or adjusted under 35 U.S.C. 154(b) by 84 days.

(21) Appl. No.: 10/267,516

(22) Filed: Oct. 9, 2002

(65) Prior Publication Data

US 2003/0087216 A1    May 8, 2003

Related U.S. Application Data

(60) Provisional application No. 60/327,847, filed on Oct. 9, 2001.

(51) Int. Cl.
 *A61C 5/12*  (2006.01)
(52) U.S. Cl. .................................. 433/139
(58) Field of Classification Search ............. 433/139, 433/153, 155, 156, 136, 137, 138, 34, 37, 433/38, 41–47; D24/181
See application file for complete search history.

(56) References Cited

U.S. PATENT DOCUMENTS

| | | | | |
|---|---|---|---|---|
| 207,103 | A | * | 8/1878 | Busey ..................... 433/139 |
| 4,986,752 | A | * | 1/1991 | Graves .................... 433/138 |
| 5,607,302 | A | * | 3/1997 | Garrison et al. ........... 433/39 |
| 5,803,734 | A | * | 9/1998 | Knutson .................. 433/136 |
| 6,039,022 | A | | 3/2000 | Meistrick et al. |
| 6,206,697 | B1 | * | 3/2001 | Hugo ...................... 433/155 |

* cited by examiner

Primary Examiner—Cary E. O'Connor (57) ABSTRACT

A rubber dam clamp comprising a transverse arch connecting two free ends, the two free ends having opposing retentive bonding pads for improved retention, stability, and comfort of rubber dam applications, when applied to a patient's tooth, due to the combination of increased contact surface and use of adhesives between the clamp and the tooth. Further, the invention relates to the adaptation of conventional rubber dam clamps into they type referred to above so as to create a similar combination of frictional force and use of adhesive in order to maintain the position of the clamp in dental procedures.

15 Claims, 6 Drawing Sheets

RUBBER DAM CLAMPS RETAINED BY ADHESION AND IMPROVED FRICTIONAL FORCES

This application claims the benefit of U.S. Provisional Application No. 60/327,847, filed Oct. 9, 2001.

BACKGROUND OF THE INVENTION

1. Field of the Invention

This invention relates to the improved design of rubber dam clamps, and more particularly to improved rubber dam clamps that retain the rubber dam in the mouth of a patient during the course of dental treatment, through the use of friction and/or adhesives.

2. Prior Art

Rubber dam clamps are commonly known in the prior art of dentistry as devices designed to apply reciprocal mechanical forces to the sides of a tooth in order to be mechanically retained in position on that tooth to restrain a rubber dam membrane. The rubber dam, is known in the prior art of dentistry as an elastic membrane designed to isolate the dentist's operative work site from the oral environment during treatment. The rubber dam is stretched over rubber dam clamps in order to be retained in position by them during treatment. The prior art of rubber dam retentive clamps is exclusively composed of mechanically retained clamps which reciprocally engage the facial and lingual surfaces of teeth, below the height of curvature of the tooth in the infra-bulge area in order to gain retention both laterally and vertically. The clamps which are widely marketed and accepted as the predominant prior art clamp are almost exclusively composed of resilient stainless steel tempered metal and are reuseable. Alternatively, rubber dam clamps manufactured of resilient plastic or composite material for repetitive or one-time use have been introduced. Despite the introduction of new materials for their construction, all true rubber dam clamps in the prior art are simple, mechanically retained devices.

One of the disadvantages and shortcomings of prior art rubber dam clamps is that they are not always stable on the tooth because they are simple mechanical devices that only approximate the contours of teeth, which vary widely in size and anatomical configuration. Prior art rubber dam clamps very often shift in position during a dental procedure, pinching the patient's gums and completely dislodge, causing the rubber dam to fail during application. When this happens, the frustrating and time-consuming task of stopping the procedure, re-applying the rubber dam clamp, and stretching the rubber dam over the clamp and an external frame must take place before resuming the operative procedure. Prior art rubber dam clamps may also be vertically unstable and are prone to rotation and tipping about an axis due to the design of their clasping components. In addition to the disadvantages of painful impingement on the patient's gums, the sharp metal clasps which contact the tooth either on enamel or cementum, the exposed dentine on the root surface, have been known to leave scratch marks or defects which later can be the focus for plaque accumulation and subsequent decay.

The prior art of rubber dam clamps is composed of simple, mechanically retained clamps that engage the tooth on the lingual and facial surfaces below the height of curvature in a region known in the dental art as the infra-bulge area. Further, U.S. Pat. No. 6,093,022, entitled Dental Dam With Integral Clamp, issued to Steven T. Swallow, Jul. 25, 2000, is the only known prior art reference to the adhesive retention of a rubber dam. The device of this disclosure is not of a true clamp, which is a separate device from a rubber dam, but rather a rubber dam with elastic projections coated with adhesive. Not only does the disclosure fail to describe a device separate from a rubber dam, there is also no true reciprocal mechanism to apply reciprocal forces in a clamping action in order to grasp an object, the tooth in this instance, in order to hold itself in position. The projections on the rubber dam, not reciprocally linked to apply tension, are simply a way of increasing and orienting surface areas of the rubber dam membrane in order to cement it directly to a tooth. Therefore, the prior art device would more appropriately be described as a rubber dam improvement.

U.S. Pat. No. 4,986,752, issued Jan. 22, 1991, to R. Gary Graves, entitled Cushioned Clamp for Securing a Dental Dam, describes a device which is a cushion composed of an elastomeric material with a slot-like recess which covers the metal clasps of a rubber dam clamp so that a portion of the cushion is compressed between the inside edge of the clamp and the tooth engaged during an application. The device is said to secure a rubber dam clamp, but makes no mention to the use of dentally compatible adhesives in order to increase retention and to stabilize the clamp during an application. In addition, the cushion, when in place, contacts a tooth in precisely the same manner in which any mechanical clamp is designed, which is to apply reciprocal forces laterally to the tooth below the height of curvature in the infra-bulge area for retention. Clamps apply retentive forces exclusively in the infra-bulge area. This results in vector forces in a cervical direction which deflect the clasps of the clamp cervically against the gingival tissues, consequently causing impingement and pain to the patient. The device is said to increase patient comfort, because the steel of the rubber dam clamp does not contact the gingival or root surface. The disclosure states "The dentist does not have to be concerned about the rubber dam clamp slipping further gingivally, . . . causing . . . the clamp to impinge on an anaesthetized gingival or cementum . . . ". The claim that a patient's comfort is increased for this reason is not accurate in that the rubber dam clamp, even with the cushion applied, is still forced against the gum tissue by reciprocal forces of the clamp deflected in a cervical direction by the inclined slope of the infra-bulge contours of the tooth. Thus the tendency for the clamp to impinge on the gingival is still present in this device. The device described in this disclosure makes no mention of the use of adhesives as a means to increase retention and stability of the clamp and to prevent the clamp from being cervically deflected and prevent impingement of the gingival tissues.

Thus a need exists for an improved rubber dam clamp that is retained by both frictional forces and adhesives in order to increase the retention and stability of the clamp during rubber dam applications.

SUMMARY OF THE INVENTION

This invention relates to the design of improved rubber dam clamps with a reciprocal clamping mechanism which are retained both mechanically by frictional forces and supplemented by the use of dentally compatible adhesives, whether manually applied by the end-user or integrally applied at the time of manufacture. The improved adhesively retained rubber dam clamps which are the subject of this disclosure may be designed for repetitive use with a one-time-use discardable consumable component for use in a single application, or may be fabricated wholly as a disposable clamp, to be discarded after a single application. An alternative embodiment of a disposable component which may be used to retro-fit a conventional rubber dam clamp in a type of field assembly of an improved rubber dam clamp is also discussed. The designs presented in this patent disclosure are of a true clamp design; i.e., for devices which are separate from the rubber dam membrane itself, with a reciprocal clamping action as in the conventional prior art to gain improved frictional retention of the clamp as well as to allow supplementary application of adhesives. In some cases, the improvement of the frictional retention alone, without the application of adhesives, will suffice in rubber dam applications, so the disclosure acknowledges use of the clamps with a purely mechanical retentive force. The disclosed clamps are applied to a tooth in a similar manner as conventional rubber dam clamps, with a spreading forceps that flexes the clamp into a wide, open position, then releases the clamp to engage a tooth. Mechanical retention is gained by the reciprocal force of the flexed resilient arch of the body of the clamp.

These and other objects of the present invention will become apparent to those skilled in the art upon reference to the following specification, drawings, and claims.

BRIEF DESCRIPTION OF THE DRAWINGS

FIG. 2 is a top view of an improved rubber dam clamp with flexible, broad-based opposing retentive pads attached to mounting plates on the free ends of the clamp FIG. 3 is an end view of an improved rubber dam clamp with flexible, broad-based opposing retentive pads attached to mounting plates on the free ends of the clamp FIG. 4 is a side view of an improved rubber dam clamp with flexible, broad-based opposing retentive pads and the mounting plates that they attach to.

DETAILED DESCRIPTION OF THE INVENTION

The invention consists of improved rubber dam clamps designed with broad-base flexible polymeric bonding pads, referred to as elastomeric pads, which increase the surface area of contact with a tooth, thereby increasing retentive frictional forces and providing a surface for the application of adhesives in order to be adhesively attached to a tooth during a dental procedure. Improved frictional contact and adhesive bonding result in a retaining clamp which resists dislodgement, cervical displacement, and torsional rotation, thus making the clamp far more stable and comfortable for a patient during application and far more reliable for the clincian during treatment procedures. The improvements which are a part of this disclosure are applicable to all varieties of rubber dam clamps, including conventional isolation rubber dam clamps and also general field isolation rubber dam clamps. While this disclosure focuses primarily on the clamps sharing the retentive mechanisms of improved frictional and adhesive retention, the clamps may also be utilized without adhesives, with the improved frictional contact surface of their flexible polymeric pads alone, or as an alternative embodiment as concave suction 'cups' for retention.

Dental adhesives that adhere to the highly mineralized structure of teeth; namely the enamel, dentin, or cementum, and are biologically compatible for oral use, are used in this application. Adhesives applied to the improved rubber dam clamps may either be manually applied by the end user prior to application, or alternatively may be integrally applied during the process of manufacture. The three general classifications of embodiments of rubber dam clamps designed for this purpose are: re-usable clamps of either metal, plastic, or composite composition with replaceable adhesive pads, disposable one time use plastic or composite rubber dam clamps with integrally attached adhesive pads, and polymeric attachments with the capacity for retrofitting existing rubber dam clamps with an adhesive interface of retention to the dentition.

Adhesive Characteristics

Due to the extensive research conducted on adhesives which attach, adhere, or bond orthodontic brackets to the hard mineralized structures of teeth, and specifically to enamel, there is a plethora of formulations available for the application of adhesively retained rubber dam clamps. Effective adhesion to enamel has been achieved with relative ease and has repeatedly proven to be reliable clinically. Early formulations for this purpose included bis-GMA, bisphenyl glycidyl dimethacrylate, and UDMA, urethane dimethacrylate. In addition, extensive research in the adhesive bonding of composite resin restorative materials has prepared the way for formulations which effectively bond to enamel and dentine has broadened the availability of formulations which are available for this purpose. Two notable classifications of formulations with this capacity are primarily dimethacrylate derivatives and glass-ionomer cements, which are the ion-leachable fluoroaluminosilicate glass of the silicate cements. Recently, these two chemical formulations have been combined as resin-modified glass-ionomer cements, with characteristics which appear promising. The research of chemical formulations, and clinical efficacy of adhesion to the mineralized hard structures of teeth is such a dynamic and rapidly evolving science, that its classification has been described as generational, rather than chemically. Hence, one generation after another replaces the approach to adhesive formulations. Therefore, the specification of a single formulation for applications involving the retention of rubber dam clamps by adhesion would be insufficiently broad to include all of the current and future options available for this application. The dentally compatible adhesives that may be suitable for this application may vary by formulation and evolve with time, but acceptable formulations will have some important material handling properties which are important to this application.

First, the adhesives which are considered acceptable are preferably biologically compatible, non-toxic, and physiologically safe to the dentition and to the patient. Second, adhesives either wholly lacking in water soluability or having a limited water soluability are chosen in order for the adhesive to remain effectively adherent during the normal course of their application in a highly aqueous environment. Treatment duration may vary from as short a period of time of 15 minutes to as long as three hours, but average appointments are generally 45 minutes to 1 hour. Third, the adhesives selected are effective in adhering to the hard, mineralized surfaces of teeth, which are enamel on the crown of the tooth, or cementum or exposed dentine on the root surface. These hard structures have both a chrystalline and an organic composition, to varying degrees depending on which material is considered. Fourth, the adhesives selected are preferably an effective adherent in the presence of some moisture, and to some degree bodily fluids. Water, saliva, and blood are the predominant fluids under consideration for this type of application. Fifth, the adhesives selected adhere with a tenacity of a magnitude sufficient to overcome the forces applied to the rubber dam clamp by the stretching of the rubber dam membrane during the course of its application. Sixth, the adhesives selected are preferably formulated in order to reversibly release the clamp when the procedure is completed, and detach from the receptor, which is either the enamel of the crown or the cementum or dentine of the root, without leaving a residual sticky residue or residual taste in the patient's mouth following treatment. Seventh, the manner in which the adhesives are applied may either be manually by the end-user or they may be integrally applied at the time of manufacture. Eighth, the manner in which the clinician activates the adhesive bond to tooth structure will generally fall under the general classifications of either pressure-sensitive adhesives, chemically activated adhesives, or photoactivated adhesives. These three classifications of activation will structure the outline of the discussion of potential chemical formulations of adhesives acceptable for this application:

1. Pressure Sensitive Adhesives

Adhesively retained rubber dam clamps may be constructed with integrally applied adhesives in the process of their manufacture. One classification of adhesives of potential for this application is known as pressure sensitive adhesives, also referred to as PSA's. Pressure sensitive adhesives are viscoelastic materials which, in free solvent form, remain permanently tacky and will adhere instantaneously to a wide variety of solid surfaces as a result of a very slight pressure. A PSA is usually applied in the form of a solvent-free coating on a 'backing', often a flexible backing, which in this application is the elastic surface of the retentive pad of the specially designed adhesive rubber dam clamp. In the present invention the PSA attaches the 'backing' material (i.e. the elastic retentive pad of the clamp) to a 'receptor' (i.e. the surface to which the PSA is to adhere to), the receptor surface being the hard mineralized surface of a tooth, whether it is composed of enamel, cementum, or exposed dentine.

The PSA necessarily has the characteristics that satisfy the requirements of the application, which in this case is adhesively retaining a rubber dam clamp. The PSA adheres to the receptor with sufficient strength' to resist accidental removal from the receptor under the conditions encountered during application, and in this case, the retaining clamp continues to retain the rubber dam in the presence of tensile forces and shear forces of the stretched elastic membrane. It also preferably adheres to the hard tissues of the teeth in the presence of oral fluids and water present upon application and continues to adhere tenaciously in the attachment phase in spite of being in a moist environment which is bathed in water and fluids. The PSA adheres for the anticipated duration of the treatment application. It is also preferable that the PSA be able to be removed cleanly from the receptor without leaving a residue of adhesive and without leaving an undesireable taste in the patient's mouth and it is further preferable to be able to remove the clamp without rupturing the 'backing' material. The PSA is hypoallergenic, non-toxic, non-irritating, and physiologically safe for the patient. Although the clamp must tenaciously adhere the clamp to the tooth during the attachment phase, it is optimum if the clamp is easily removed by finger pressure or by instrument at the completion of the procedure.

The integrally applied adhesive substance may be in the form of a viscous liquid, gel, solution, or other form in a substantially uniform continuous coating when applied to the retentive pads of the rubber dam clamp. Pressure sensitive adhesives are generally covered by an easy to remove covering called a release liner, which helps keep the adhesive in a maximally tacky state until it is required for use, at which time the release liner is stripped off, exposing the adhesive, and applied to the hard structures of a tooth. The release liner may be composed of a number of a number of flexible thin sheet materials such as polyethylene, paper, polyester, or other material coated with a non-stick type of material. Thus the release liner exhibits less affinity for the adhesive than the backing to which it is attached, leaving the adhesive on the backing upon removal of the liner. Some common coatings of release liners are Teflon, wax, silicone, fluoropolymers, or other types of non-stick materials. Other types of release agents may be found in Kirk-Othmer Encyclopedia of Chemical Technology, $4^{th}$ Edition, Volume 21, pp. 207–218, incorporated herein as a reference.

2. Chemically Activated Adhesives

This classification of adhesives may be activated by the application of chemical agents with potential for this application might include agents activated by water or the components of saliva. The embodiment of an adhesive clamp allows the dentist to simply spray water over the adhesive surfaces of the bonding pads with an air-water syringe, which is standard equipment in a dental office. The clamp would then be placed in position while the adhesive cured or polymerized to maximal adherent strength.

3. Photo-Activated Adhesives

Another classification of adhesives commonly used in dentistry are photo-activated adhesives in which the process of polymerization and activation of the adhesive is initiated by the application of light of a specified wavelength. Current practice of modem dentistry includes an abundance of light cured composite filling materials and other photo-activated products, so most dental offices are equipped with light curing devices. An embodiment of adhesively retained rubber dam clamps with photo-activated adhesives applied to transparent or translucent bonding pads will allow the dentist to place a clamp on a tooth and then light cure the adhesive to maximal adherent strength in a matter of seconds in order to retain a rubber dam.

The Strength of the Adhesive Bond

There are a number of factors that affect the tenaciousness of the adhesive bond in this application. First it should be recognized that retention of these clamps is derived not just from the adhesive bonding alone, but instead from a combination of improved frictional forces of the clamping action of the device and the adhesive bond acting in concert with one another. The increased contact surface of the retentive pad increases the surface area of contact resulting in increased retentive frictional forces. In addition, the contact surface provides a platform for the application of adhesives for bonding with the surface of a tooth. Since the retentive pads are located on both ends of the clamp, the total surface area for either the generation of frictional forces or for providing a total area of adhesive contact must be additive for the two pads. The variables of total area of contact multiplied by the retentiveness of a given adhesive and the frictional forces generated from the clamping action of the transverse resilient arch, need to exceed the summation of tensile forces of the stretched rubber dam membrane in order to retain the clamp and the rubber dam in the mouth in order to be effective.

Preferred Embodiments

Figure 1:
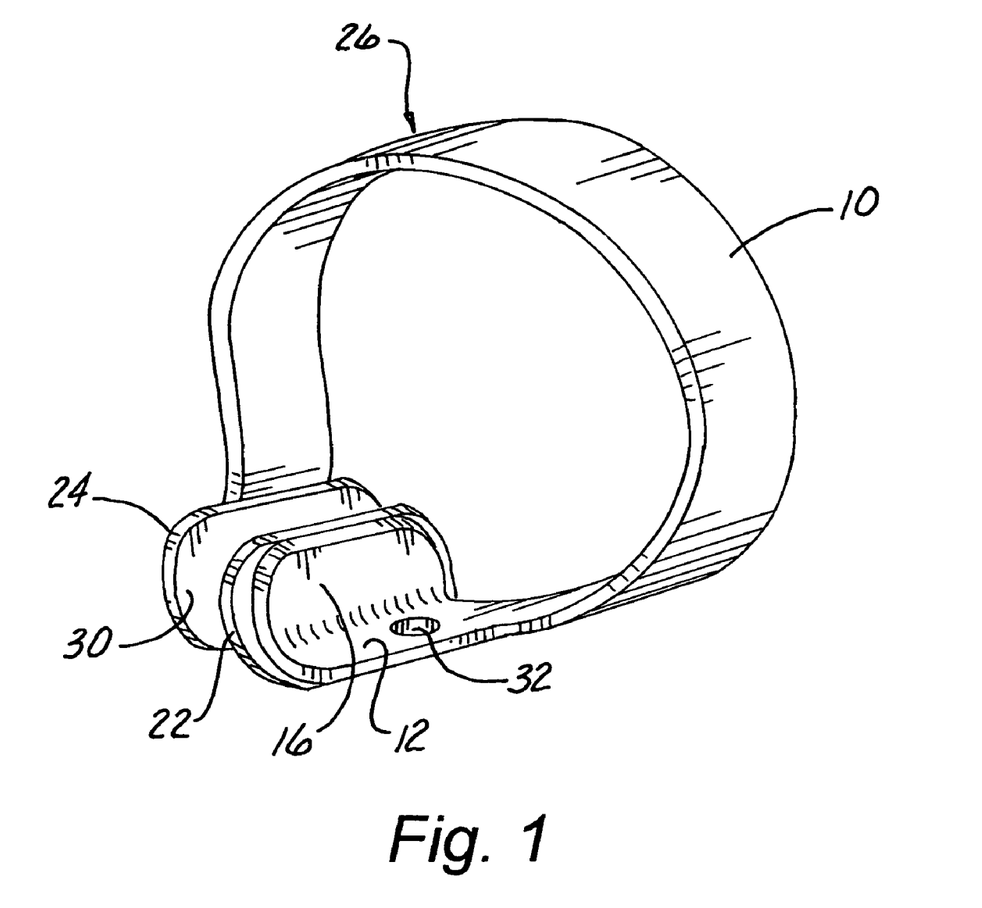
FIG. 1 is an isometric view of an improved rubber dam clamp with flexible, broad-based opposing retentive pads attached to mounting plates on the free ends of the clamp
Figures 2, 3, 4:
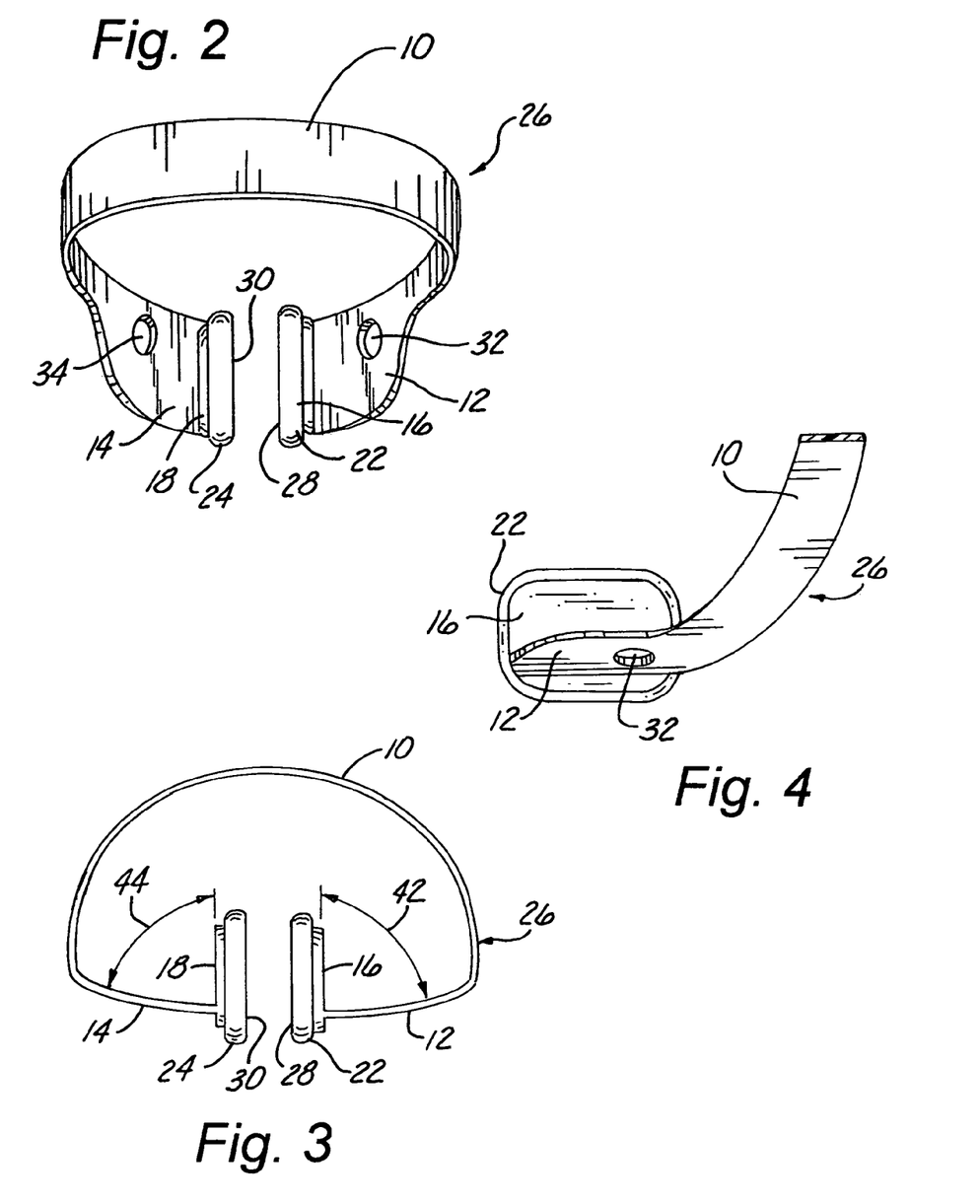

The representative view of the preferred embodiment of the clamp 26, the improved conventional rubber dam clamp 26 shown generally in an isometric view in FIG. 1, demonstrates a resilient transverse arch 10 which flexes when the clamp 26 is spread open with a rubber dam forceps (not shown). FIG. 2 is a top view of the clamp 26 showing that on both ends of the transverse arch 10 are free ends 12 and 14, to which a mounting plates 16 and 18 are integrally mounted. FIG. 3 demonstrates that the mounting plates 16 and 18 are mounted to the free ends 12 and 14 of the clamp at an angle of incidence 42 and 44 which may either be a right angle, as shown in the drawing, or an acute angle or obtuse angle. The angle of incidence 44 of the angle of the mounting plate 18 to the free end 14 of the clamp 26 on the left side of the clamp 26 is independent of the angle of incidence 42 of the angle on the right side of the clamp 26 and is determined by the anatomical requirements of the contours of the tooth 20 to be clamped. The mounting plates 16 and 18 serve to attach flexible, polymeric bonding pads 22 and 24 to the mounting plates 16 and 18 in such a manner that the contact surfaces 28 and 30 are inclined at the angle of the mounting plates 16 and 18 for contact with a tooth 20 to be clamped. The contact surfaces 28 and 30 face inward toward the midline of the clamp 26 in a manner in which they directly oppose one another. Located within each of the free ends 12 and 14 of the clamp 26, are forcep engaging holes 32 and 34, which serve to allow rubber dam forceps (not shown) to engage each of the free ends 12 and 14 of the clamp 26 in order to spread the free ends 12 and 14 apart by flexing the resilient transverse arch 10 of the body of the clamp 26.

Figure 5:
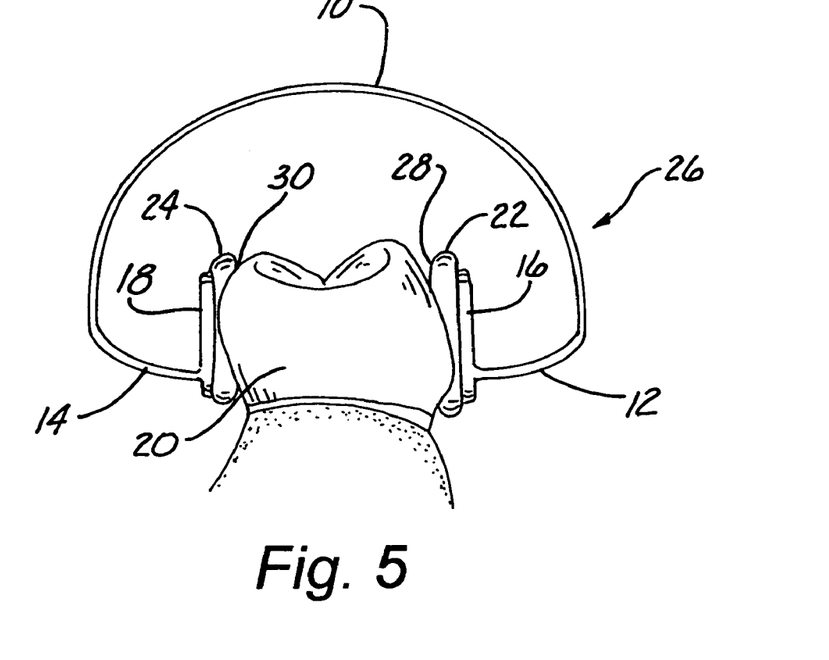
FIG. 5 is an end view of an improved rubber dam clamp engaging the facial and lingual surfaces of a tooth, demonstrating that flexible, compressible retentive pads adapt to the anatomical contours of a tooth with pressure, thereby increasing the surface contact between the clamp and the tooth
Figure 6:
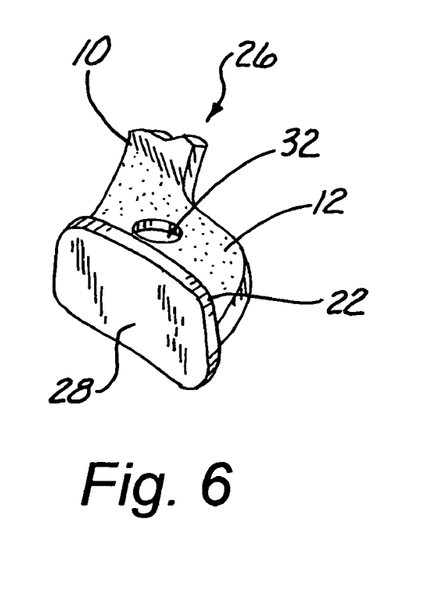
FIG. 6 is a detailed view of a flexible retentive pad with an adhesive applied to the contact surface
Figure 7:
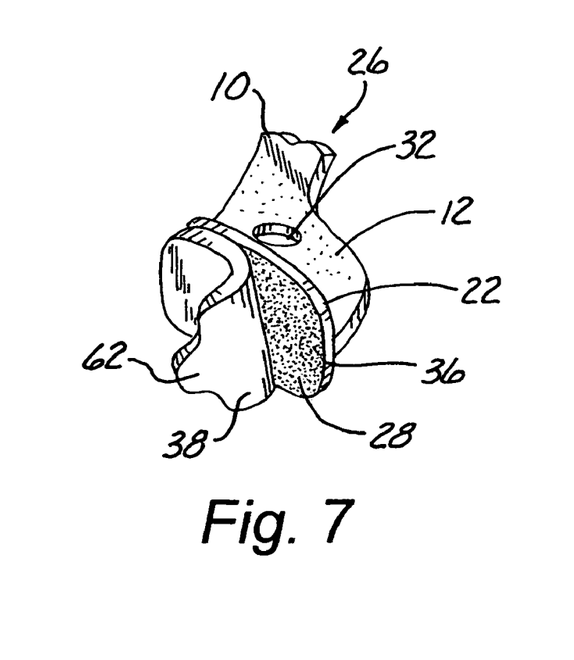
FIG. 7 is a detailed view of a flexible retentive pad with an adhesive applied to the contact surface and a release liner adhering to the adhesive layer

FIG. 4 shows a side view of the clamp 26 with a visible forcep engaging hole 32. Also seen in FIG. 4 is a flexible polymeric bonding pad 22 mounted to a mounting plate 16. The flexible bonding pads 22 and 24 may be mounted either by adhesion or by a number of variable mechanical means. These bonding pads 22 and 24 may either be integrally mounted to the mounting plates 16 and 18, as in the case of disposable, 'one-time-use' clamps 26, or alternatively may be removeably mounted to clamps 26 which are reusable. In the latter case, the flexible polymeric bonding pads 22 and 24 may be either reusable or disposable. The contact surfaces 28 and 30, so named because they contact the tooth 20 when the clamp 26 is applied and in position, are broad-based contact surfaces in order to increase the surface area of contact with the tooth 20 and thus increase the frictional forces of retention of the clamp 26. The broad-based contact surfaces 28 and 30 also serve as a surface for the application of adhesives for the bonding of the clamp 26 to the surfaces of the tooth 20. These contact surfaces 28 and 30, if fabricated without adhesives, serve to apply effective frictional forces for retention and stabilization of the clamp 26. FIG. 6 and FIG. 7 both show the free end 12 of an improved rubber dam clamp 26 with a flexible polymeric bonding pad 22 attached to the free end 12, with a layer of adhesive 36 applied to the contact surface 28 of the polymeric pad 22. FIG. 6 shows the layer of adhesive 36 applied without a release liner. FIG. 7 shows a release liner 38 partially peeled back from the layer of adhesive 12 which is applied to the contact surface 28 of the polymeric pad 22. FIG. 5 shows the flexible polymeric bonding pads 22 and 24, with their contact surfaces 28 and 30, actively engaging the facial and lingual surfaces of a tooth 20. From FIG. 5 it can be seen that pressure of the flexed transverse arch 10 of the clamp 26 has compressed the bonding pads 22 and 24 against the tooth 20 at the contacting surfaces 28 and 30 compressing the pad 22 and 24 and thus adapting the pads 22 and 24 to the contours of the surfaces of the tooth 20. In this manner, the clamps 26 may conform to a variety of different contours found in a cross-section of the population.

There will be a need for an additional adaptive mechanism for different teeth to be clamped. Just as a variety of conventional rubber dam clamps have evolved to adapt to different anatomical needs, the improved rubber dam clamps of this disclosure may vary in the angulation of the mounting of the bonding pads 22 and 24, with respect to the free ends 12 and 14 of the clamps 26. This may be achieved by varying the angulation of the mounting plates 16 and 18 to the free ends 12 and 14 of the clamp 26. Stated simply, the angle of incidence 42 and 44 of the mounting plates 16 and 18 to the free ends 12 and 14 may either be an acute angle or a right angle or an obtuse angle, in order to direct the mounting of the bonding pads 22 and 24, and ultimately the inclination of the contact surfaces 28 and 30, with respect to the final angulation of the surface of the tooth 20 to be contacted in an application.

Alternative Embodiments

Figure 8:
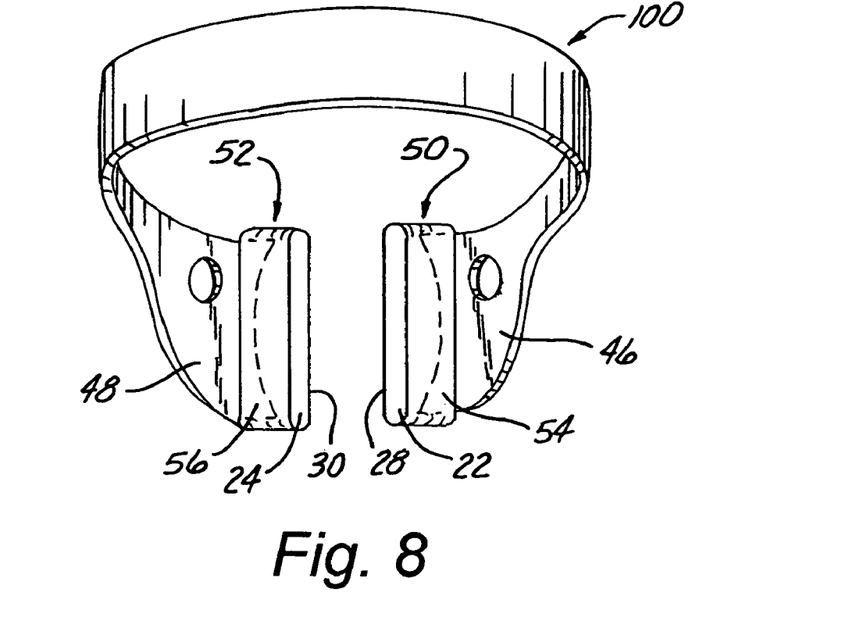
FIG. 8 is a top view of a conventional rubber dam clamp retro-fitted with two opposing flexible polymeric adhesive attachment pads
Figure 9:
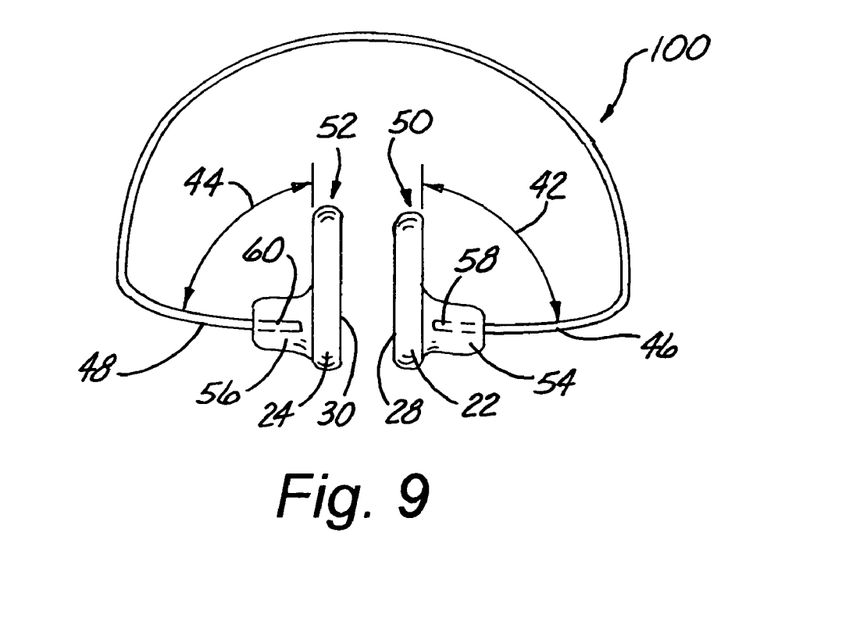
FIG. 9 is an end view of a conventional rubber dam clamp retro-fitted with two opposing flexible polymeric adhesive attachment pads
Figure 10:
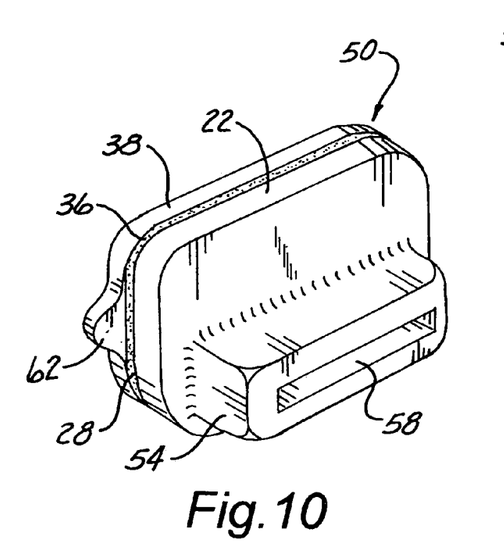
FIG. 10 is an isometric view of a flexible polymeric attachment pad showing the slotted recess which is fits over the free end of a conventional rubber dam clamp
Figure 11:
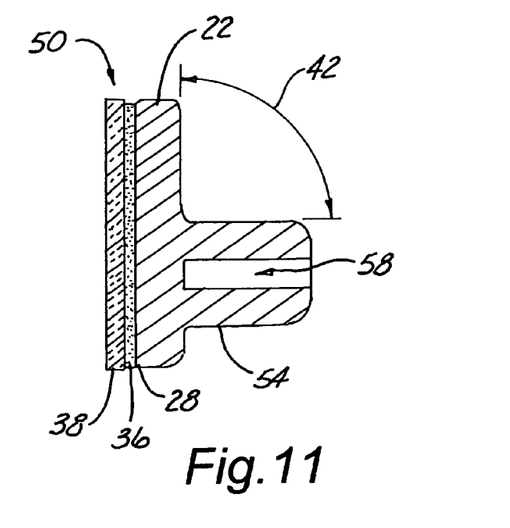
FIG. 11 is a sectional view of a flexible polymeric adhesive attachment pad showing the free end of a conventional rubber dam clamp inserted into the slotted recess of the pad. This view also shows a cross section of the whole attachment pad with a layer of adhesive and a release liner covering the adhesive layer
Figure 12:
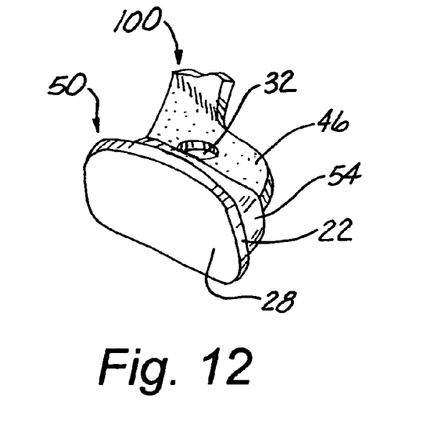
FIG. 12 is an isometric view of an adhesive attachment pad engaging the free end of a conventional rubber dam clamp with a layer of adhesive covering the contact surface of the bonding pad
Figure 13:
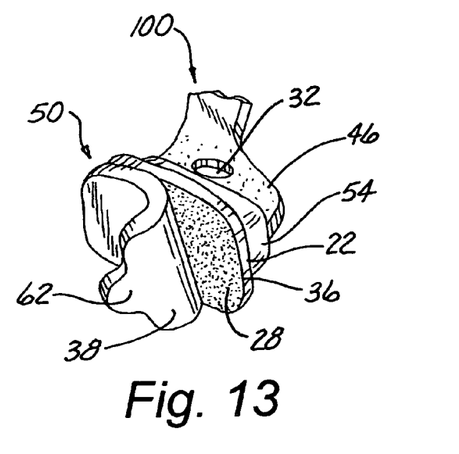
FIG. 13 is an isometric view of an adhesive attachment pad engaging the free end of a conventional rubber dam clamp with a release liner covering the layer of adhesive on the contact surface of the bonding pad

An alternative embodiment of the invention involves retro-fitting existing conventional rubber dam clamps 26 with the broad-based elastomeric pads of the disclosure. All of the features and functions of these flexible polymeric adhesive attachment pads is analogous to the primary disclosure of the reusable and disposable clamps 26 except in the manner in which these attachment pads attach to pre-existing conventional clamps 100. FIG. 8 is a top view of two polymeric attachment pads, 50, 52 attached to the free ends 46 and 48 of the conventional rubber dam clamp, 100. This view shows the flexible bonding pads 22 and 24, integrally linked to their respective mounting bases 54 and 56. The inserted free ends, 46 and 48 of the conventional rubber dam clamp 100 are shown in hidden lines engaging the mounting bases 54 and 56 of the polymeric attachment pads 22 and 24. FIG. 9 is an end view of the two polymeric attachment pads 50, 52 attached to the free ends 46, 48 of the clamp 100. This view shows the flexible bonding pads 22 and 24 each integrally linked to their respective mounting bases 54 and 56 as in the previous view. Each opposing polymeric bonding pad 22, 24 has a contact surface 28, 30 facing inward toward the midline of the clamp 100. The inserted free ends 46 and 48 of the conventional rubber dam clamp 100 are shown in hidden lines engaging slotted recesses 58 and 60 located within the mounting bases 54 and 56 of the polymeric attachment pads 50 and 52. FIG. 10 shows an isometric view of the right polymeric attachment pad 50, showing the mounting base 54 with a slotted recess 58 located longitudinally within the mounting base 54 at a right angle to the bonding pad 22. This view also shows the broad-based bonding pad 22 with a layer of adhesive 36 applied to its contact surface 28 and a release liner 38 removeably attached to the adhesive layer 36. A finger tab 62 which is a projection of the release liner 38 allows the end-user to start peeling the release liner 38 off of the adhesive prior to use. FIG. 11 is a cross-sectional view of the same polymeric attachment pad 50 engaged to the free end 46 of a conventional rubber dam clamp 100, inserted within the slotted recess 58 within the mounting base 54. This view also shows a layer of adhesive 36 applied to the contact surface 28 of the retentive bonding pad 22 and a release liner 38 attached to the layer of adhesive 36. Although the bonding pad 22 shown is attached to the mounting base 54 in such a way that the long axis of the slotted recess 58 is at a 90 degree angle, these bonding pads 22 may alternatively be mounted at an angle of incidence 42 of either an acute angle or a right angle or an obtuse angle so as to direct the inclination of the contact surface 28 with respect to the desired angle of inclination for a given application. FIG. 12 shows a retentive bonding pad 22 with its contact surface 28 linked to its mounting base 54 engaging the free end 46 of a conventional rubber dam clamp 100, and no adhesive is applied to the surface. FIG. 13 shows a retentive bonding pad 22 with a layer of adhesive 36 applied to the contact surface 28 and a release liner 38 with a finger tab 62. The bonding pad 22 is linked to its mounting base 54 which is engaged to the free end 46 of a conventional rubber dam clamp 100.

Figure 14:
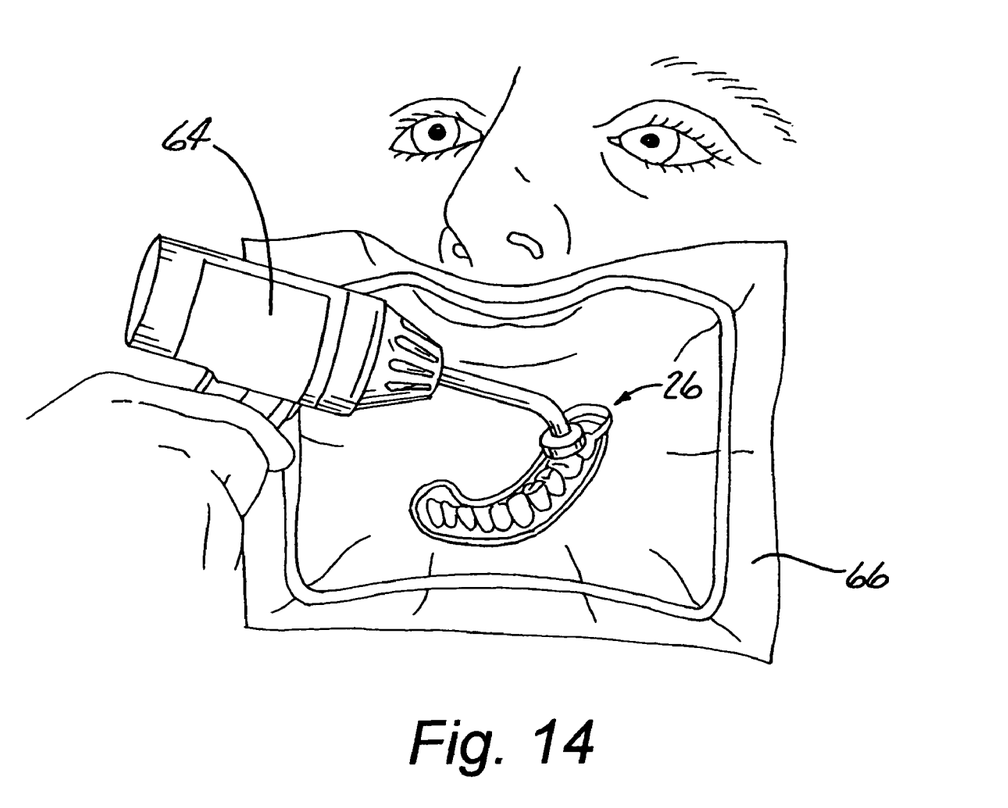
FIG. 14 is a drawing of a standard dental curing light activating a photo-activated adhesive polymer which has been applied to the contact surface of an improved rubber dam clamp in order to bond it to the tooth surface

FIG. 14 demonstrates the use of a standard dental curing light 64 shining light of a specified wavelength on a photo-activated adhesively retained rubber dam clamp 26, to retain a rubber dam 66 in the mouth of a patient during dental treatment.

The foregoing description and drawings comprise illustrative embodiments of the present inventions and it is to be realized that the general relationships for the parts of the invention are illustrative of the function and manner of operation of said invention, and the assembly and use of the invention. Equivalent relationships to those illustrated in the drawings and described in the specifications expressing variations in size, materials, shape, form, function, and manner of operation, but which describe equivalent relationships to those illustrated in this disclosure are to be considered to be within the spirit and scope of the invention, and may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. For example, since numerous modifications and changes will readily occur to those skilled in the art, it is not desired to limit the invention to the exact construction and operation shown and described, and accordingly, all suitable modifications and equivalents may be resorted to by the inventor, as falling with the spirit and scope of the invention. By way of example, although the retentive bonding pads are shown as being essentially flat on their contact surfaces, these retentive pads might also be fabricated as being concave and still be within the spirit and scope of the disclosure. Although the disposable retentive pads show an adhesive on one surface for bonding to a tooth, equivalent pads might have an adhesive applied to both surfaces, for bonding to a tooth and also for being removeably bonded to the mounting plates of a clamp. Simple mechanical mechanisms which would allow a retentive bonding pad to be mechanically attached to a mounting plate, or variations in size of retentive pads and variations of inclination of the retentive pads and their respective contact surfaces in order to adapt to different teeth in the mouth to be clamped, should also be considered to be within the spirit and scope of the disclosure. Variations of clamp design, such as cervical retraction rubber dam clamps for general field isolation should also be considered to be within the spirit and scope of this disclosure.

It should be readily apparent and obvious to one skilled in the art of dentistry that occasions may arise when only one adhesive retentive pad would be advantageous, while the reciprocal free end is devoted to a specialized function. An example of this would be a #212 clamp where the lingual free end would have an adhesive pad, while the labial free would have a mechanical means of retracting the gingival. It should also be readily apparent that while adhesive retention has been given great emphasis in this disclosure, these clamps, with their broad-based contact surfaces which significantly improve frictional forces of retention, will sometimes be efficaciously for their improved frictional retentive qualities without the use of adhesives. The improved adhesive rubber dam clamps of this disclosure are preferably ligated before insertion into the mouth in order to prevent accidental swallowing or aspiration of the clamp. This alternative use should be considered to be fully within the spirit and scope of this disclosure.

I claim:

1. A clamp for retaining a rubber dam in a desired position relative to a tooth of a patient, comprising:
    (a) transverse arch connecting two free ends;
    (b) opposing retentive bonding pads associated with the two free ends and arranged in an opposing relationship for improved retention, stability, and comfort of rubber dam applications; and
    (c) when applied to a patient's tooth, the bonding pads engage at least one-half of the facial and lingual surfaces of the tooth.

2. A rubber dam clamp as defined in claim 1, wherein the bonding pads are comprised of a flexible, elastomeric, and retentive material for increasing a contact surface between the clamp and the tooth.

3. A rubber dam clamp as defined in claim 2, wherein adhesives are applied to the contact surface of the retentive pads in order to increase the retention and stability of the clamp engaging the tooth.

4. A rubber dam clamp as defined in claim 3, wherein the adhesives are applied manually by an end user or integrally applied during manufacture.

5. A rubber dam clamp as defined in claim 3, wherein the adhesives are selected to adhere to hard mineralized structures of the tooth, such as enamel, cementum, or dentine.

6. A rubber dam clamp as defined in claim 3, wherein the adhesives applied are selected from the group consisting of pressure sensitive adhesives, chemically activated adhesives, and photo-activated adhesives.

7. A rubber dam clamp as defined in claim 3, wherein the adhesives applied are of a composition lacking water solubility or having limited water solubility.

8. A rubber dam clamp as defined in claim 3, wherein the adhesive strength is selected to be inversely proportional to retention provided by mechanical forces of the clamp.

9. A rubber dam clamp as defined in claim 2, wherein the retentive pads are comprised of a material that is selected from the group consisting of transparent, translucent, and opaque materials.

10. A rubber dam clamp as defined in claim 2, wherein the retentive pads are comprised of a material to facilitate transmission of light through the elastomeric pad to a photo-activated adhesive on the contact surface.

11. A rubber dam clamp as defined in claim 1, wherein the bonding pads increase frictional forces between the clamp and the tooth, thereby improving retention and stability.

12. A rubber dam clamp as defined in claim 1, wherein the bonding pads provide a surface area for the application of an adhesive, thereby allowing for adhesive retention of the clamp to the tooth.

13. A rubber dam clamp as defined in claim 1, wherein the bonding pads serve as a barrier to protect the tooth from scratching or damage from the clamp and to protect the gingival tissues of the patient from the clamp.

14. A rubber dam clamp as defined in claim 2, wherein the flexible retentive pads allow adaptation of the clamp to varying anatomic contours of individual teeth.

15. A rubber dam clamp as defined in claim 1, wherein the clamp is made from a material composition selected from the group consisting of metals, alloys of metals, stainless steel, polymers, plastic and composite materials.

* * * * *